United States Patent
Kitada (10) Patent No.: US 10,627,384 B1
(45) Date of Patent: Apr. 21, 2020

(54) WATER QUALITY ANALYZER

(71) Applicant: SHIMADZU CORPORATION, Kyoto-shi, Kyoto (JP)

(72) Inventor: Yoshio Kitada, Kyoto (JP)

(73) Assignee: SHIMADZU CORPORATION, Kyoto-shi, Kyoto (JP)

(*) Notice: Subject to any disclaimer, the term of this patent is extended or adjusted under 35 U.S.C. 154(b) by 0 days.

(21) Appl. No.: 16/295,585

(22) Filed: Mar. 7, 2019

(51) Int. Cl.
  *G01N 33/18* (2006.01)
  *G01N 1/10* (2006.01)
  *G01N 21/59* (2006.01)

(52) U.S. Cl.
  CPC .............. *G01N 33/188* (2013.01); *G01N 1/10* (2013.01); *G01N 21/59* (2013.01); *G01N 33/1826* (2013.01)

(58) Field of Classification Search
  CPC .................................................. G01N 33/188
  USPC ......................................................... 356/442
  See application file for complete search history.

(56) References Cited

U.S. PATENT DOCUMENTS

| | | | |
|---|---|---|---|
| 4,517,302 A | 5/1985 | Saros | |
| 5,013,488 A * | 5/1991 | Abadi | G01N 9/14 137/91 |
| 7,311,818 B1 * | 12/2007 | Gurfinkel | B01D 21/2444 210/96.1 |
| 7,504,028 B1 * | 3/2009 | Gurfinkel | B01D 21/245 210/170.11 |
| 2007/0254374 A1 * | 11/2007 | Iharada | G01N 33/1846 436/146 |
| 2011/0176976 A1 * | 7/2011 | Ebi | G01N 35/04 422/547 |
| 2017/0197845 A1 * | 7/2017 | Hashimoto | C02F 1/725 |
| 2018/0364152 A1 * | 12/2018 | Naor | G01N 21/01 |

FOREIGN PATENT DOCUMENTS

| | | |
|---|---|---|
| JP | 57-101981 U | 6/1982 |
| JP | 59-92356 A | 5/1984 |
| JP | 2003-344381 A | 12/2003 |
| JP | 2004-184162 A | 7/2004 |
| JP | 2009-186365 A | 8/2009 |
| JP | 2016-80441 A | 5/2016 |

OTHER PUBLICATIONS

Notice of Reasons for Refusal dated Dec. 3, 2019 issued by the Japanese Patent Office in counterpart Application No. 2016-167570.

* cited by examiner

*Primary Examiner* — Tarifur R Chowdhury
*Assistant Examiner* — Omar H Nixon
(74) *Attorney, Agent, or Firm* — Sughrue Mion, PLLC (57) ABSTRACT

The invention provides a water quality analyzer with which an abnormality in the collection of water can be determined by detecting whether or not a predetermined amount of a liquid sample has been fed into a sample container. The analyzer is formed of: a sample container 53 into which a liquid sample can be introduced through a liquid sample introduction port 53e formed in a lower portion of the container 53; a light source unit 51 for irradiating the container 53 with light; and a detection unit 52 for detecting light that has passed through the container 53, and further includes a determination unit for determining whether or not a predetermined amount of the liquid sample has been contained in the container 53 on the basis of the change in the light intensity detected by the detection unit 52 when the liquid sample is fed into the container 53.

4 Claims, 5 Drawing Sheets

Prior Art

FIG. 5

WATER QUALITY ANALYZER

BACKGROUND OF THE INVENTION

1. Field of the Invention

The present invention relates to a water quality analyzer, and in particular, to a total nitrogen measuring device for measuring the total nitrogen concentration in a liquid sample.

2. Description of Related Art

As for the method for measuring the total nitrogen where the total amount of total nitrogen compounds in a liquid sample such as industrial wastewater is represented by the concentration of nitrogen, the "ultraviolet spectrophotometric method" (JIS K 0102 45.2) that is prescribed in the "testing methods for industrial wastewater" according to the Japanese Industrial Standard is generally used. According to the ultraviolet spectrophotometric method, a liquid sample to which potassium peroxydisulfate, which is an oxidizing agent, is added is processed through autoclaving, that is to say, at a high temperature and under high pressure.

In addition, a total nitrogen measuring device is commercially available where a method gained by combining "UV photo-oxidation decomposition" with the "ultraviolet spectrophotometric method" (hereinafter, referred to as "UV photo-oxidation decomposition method") is adopted.

In accordance with the UV photo-oxidation decomposition method, a predetermined amount (a) of a liquid sample S that has been collected is first weighed and diluted with a predetermined amount (b) of diluent water. Then, as a pre-process for alkalizing the liquid sample S so that the nitrogen compounds in the liquid sample S can be easily decomposed, a predetermined amount (c) of a sodium hydroxide solution (NaOH) is added. Next, a predetermined amount (d) of a potassium peroxydisulfate solution, which becomes an oxidizing agent, is added, and after that, a predetermined amount (a+b+c+d) of the prepared liquid sample S1 is transferred to the UV photo-oxidation decomposition process.

Next, the prepared liquid sample S1 is irradiated with ultraviolet rays under the conditions of being heated at 70 degrees or higher so as to be converted to a reacted liquid sample S2 where the nitrogen compounds in the prepared liquid sample S1 has reacted with the ultraviolet rays and oxidatively decomposed to nitrate ions. After that, a predetermined amount (e) of hydrochloric acid or the like for adjusting the pH is added at the time when the absorbance is determined, and thus, the total nitrogen concentration in a predetermined amount (a+b+c+d+e) of the prepared liquid sample S3 is measured through the determination of absorbance in the vicinity of 220 nm (see Patent Literature 1).

Figure 2:
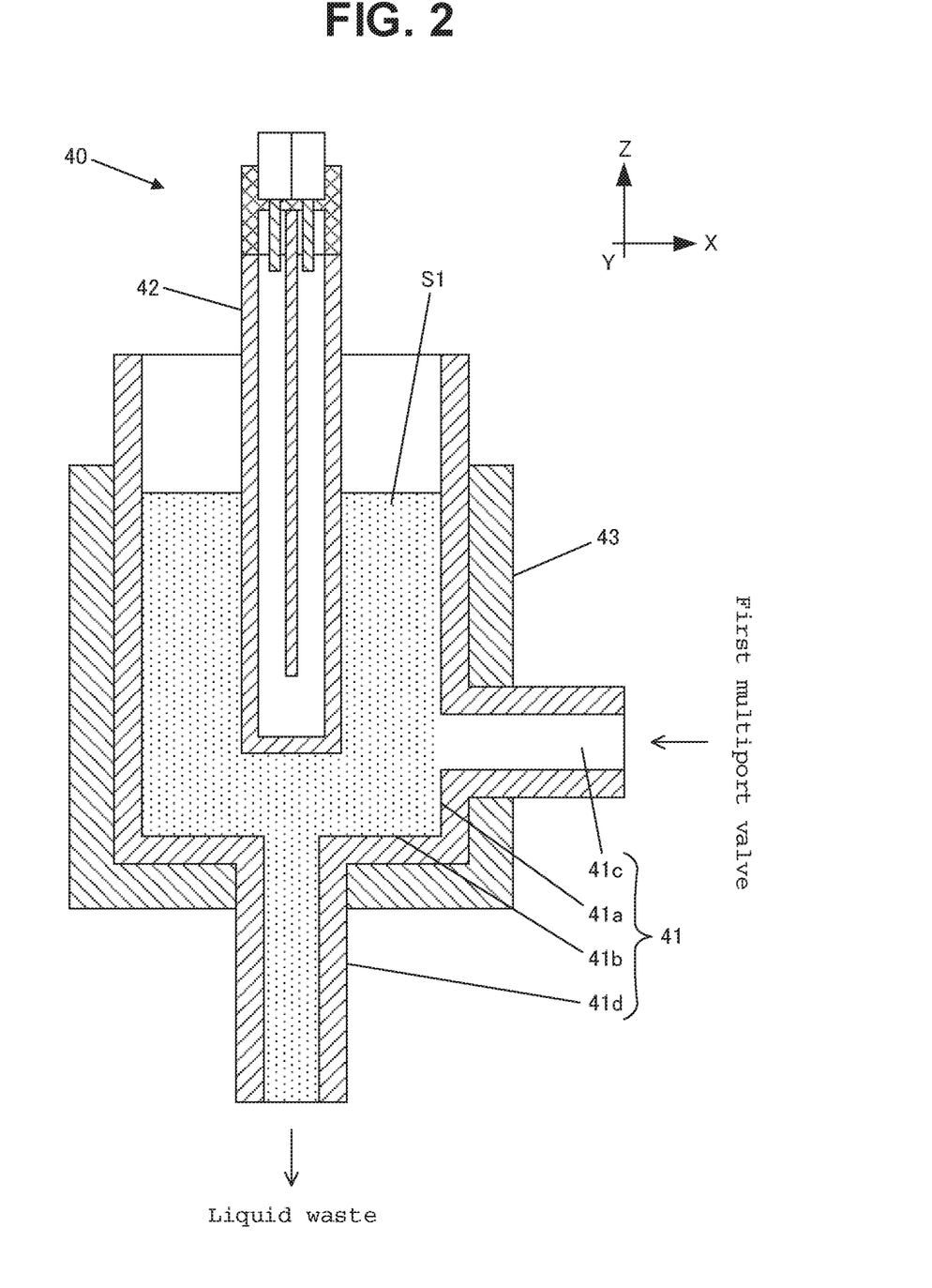
FIG. 2 is a cross-sectional diagram showing an example of the configuration of the reactor.
Figure 3:
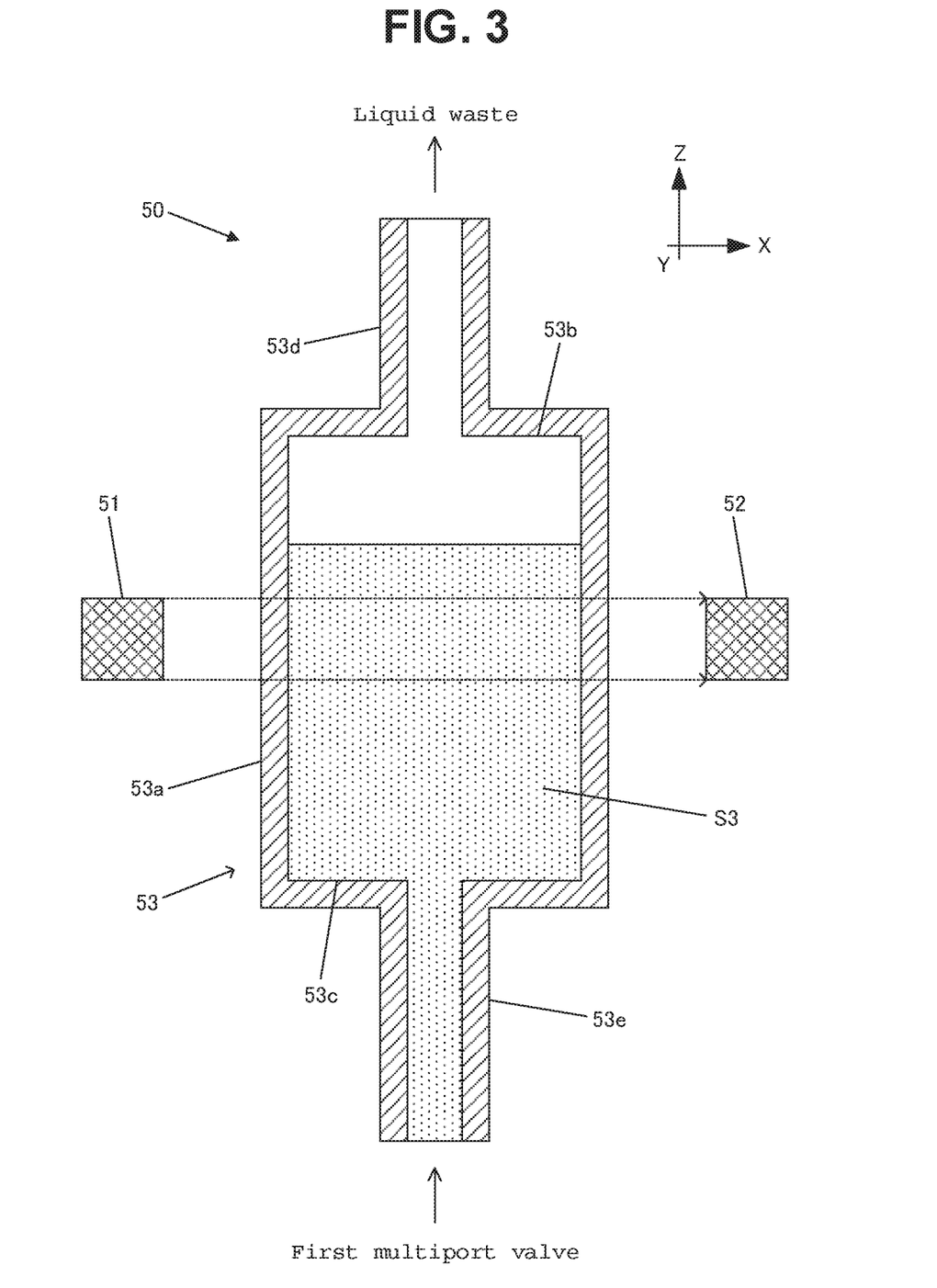
FIG. 3 is a cross-sectional diagram showing an example of the configuration of the measuring unit.
Figure 4:
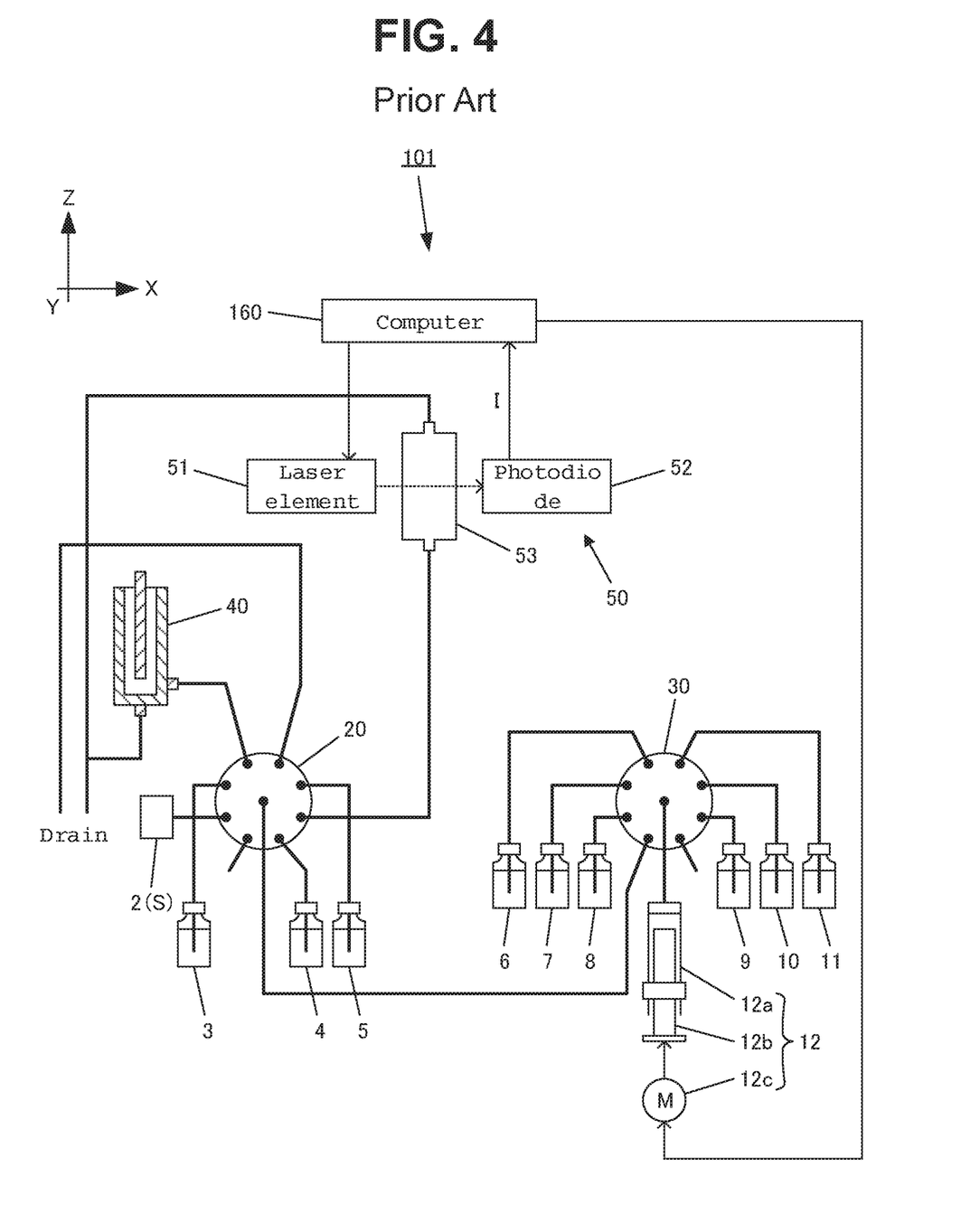
FIG. 4 is a schematic diagram showing the entire configuration of an example of a conventional total nitrogen measuring device.

FIG. 4 is a diagram schematically showing an example of the entire configuration of a conventional online total nitrogen measuring device. FIG. 2 is a cross-sectional diagram showing an example of the configuration of a reactor, and FIG. 3 is a cross-sectional diagram showing an example of the configuration of a measuring unit. Here, one direction that is horizontal relative to the ground is direction X, the direction that is horizontal relative to the ground and perpendicular to the direction X is direction Y, and the direction that is perpendicular to the direction X and direction Y is direction Z.

An online total nitrogen measuring device 101 is provided with a sample tank 2, a syringe pump (weighing unit) 12, a first multiport valve 20, a second multiport valve 30, a reactor 40, a measuring unit 50 and a computer 160.

A liquid sample S such as industrial wastewater or environmental water is continuously supplied to the sample tank 2, which is connected to one distribution port of the first multiport valve 20.

The syringe pump 12 is provided with a syringe 12a having a cylindrical body, a piston 12b in columnar form that is inserted into the syringe 12a and a pulse motor 12c that is controlled by the computer 160. Thus, the piston 12b of the syringe pump 12 is moved upwards and downwards by the pulse motor 12c. When the piston 12b is drawn downwards, a predetermined amount of solution is injected into the syringe 12a, and when the piston 12b is pushed upwards, the predetermined amount of solution within the syringe 12a is discharged.

The first multiport valve 20 is made up of eight distribution ports and one common port. The sample tank 2, a container 3 containing Span liquid, a container 4 containing a standard liquid sample, a container 5 containing diluent water, the reactor 40 and the measuring unit 50 are connected to the distribution ports. In addition, the first multiport valve 20 is driven by a motor (not shown) so as to connect the common port to one selected distribution port.

The second multiport valve 30 is made of eight distribution ports and one common port. A container 6 containing a potassium peroxydisulfate solution, a container 7 containing a sodium hydroxide solution, a container 8 containing hydrochloric acid, a container 9 containing molybdic acid, a container 10 containing ascorbic acid, a container 11 containing sulfuric acid, and the common port of the first multiport valve 20 are connected to the distribution ports. Furthermore, the syringe pump 12 is connected to the common port of the second multiport valve 30. In addition, the second multiport valve 30 is driven by a motor (not shown) so as to connect the common port to one selected distribution port.

As shown in FIG. 2, the reactor 40 is provided with a reaction container 41 for containing a prepared liquid sample S1, an ultraviolet ray lamp 42 for irradiating the prepared liquid sample S1 with ultraviolet rays, and a heater 43 for controlling the temperature for oxidation reaction of the prepared liquid sample S1.

The reaction container 41 is made of a sidewall 41a in a cylindrical form (outer diameter: 12 mm, inner diameter: 10 mm, height: 130 mm, for example), and a circular bottom 41b, where a liquid sample introduction port 41c that is connected to the first multiport valve 20 is created in the lower portion of the sidewall 41a, and a liquid sample discharge port 41d that is connected to the drain for disposing of liquid waste is created on the bottom 41b. Here, the reaction container 41 is formed of crystal glass or the like.

The heater 43 is provided with a cylindrical block body made of a metal and a thermocouple (not shown) that is buried in the block body and is arranged so as to make contact with the outer peripheral surface of the reaction container 41.

The ultraviolet ray lamp 42 is a low pressure mercury lamp, an excimer lamp, a deuterium lamp, a xenon lamp or an Hg—Zn—Pb lamp, for example.

The ultraviolet ray lamp 42 is inserted from the top so as to be arranged in the center portion within the reaction container 41. As a result, when a predetermined amount of the prepared liquid sample S1 is contained within the reaction container 41, the ultraviolet ray lamp 42 is immersed in the prepared liquid sample S1.

As shown in FIG. 3, the measuring unit 50 is provided with a semiconductor laser element (light source unit) 51 for emitting a laser beam to the right (direction X), a photodiode (detection unit) 52 for detecting the light intensity I of the laser beam that progresses in the direction X, and a measuring cell (sample container) 53 for containing a predetermined amount of the prepared liquid sample S3 that is arranged between the semiconductor laser element 51 and the photodiode 52. Here, the light source unit may not necessarily be a semiconductor laser element, but may be a xenon flash lamp or the like.

The measuring cell 53 is made of a sidewall 53a in cylindrical form (outer diameter: 12 mm, inner diameter: 10 mm, height: 130 mm, for example), a circular top 53b and a circular bottom 53c, where a liquid sample discharge port 53d that is connected to the drain for disposing liquid waste is created in the top 53b, and a liquid sample introduction port 53e that is connected to the first multiport valve 20 is created on the bottom 53c. Here, the measuring cell 53 is formed of crystal glass or the like.

As a result, the laser beam that has emitted from the semiconductor laser element 51 passes through the sidewall 53a, passes through a region to be measured (light path), passes through the sidewall 53a on the opposite side, and after that is received by the photodiode 52. At this time, the laser beam is partially absorbed by a prepared liquid sample S3 in the case where the prepared liquid sample S3 is in the region to be measured.

Here, a method for automatically analyzing the total nitrogen concentration of a liquid sample S by using the above-described online total nitrogen measuring device 101 is described. The computer 160 outputs a drive signal to the pulse motor 12c in accordance with a predetermined timing, and thereby a predetermined amount (a) of a liquid sample S is weighed and collected from the sample tank 2 by the syringe pump 12. A drive signal is again outputted to the pulse motor 12c, and thereby a predetermined amount (b) of diluent water is weighed and collected from the container 5 by the syringe pump 12 so that the liquid sample S is diluted within the syringe 12a. Next, the computer 160 outputs a drive signal to the pulse motor 12c, and thereby a predetermined amount (c) of a potassium hydroxide solution in the container 7 and a predetermined amount (d) of a potassium peroxydisulfate solution in the container 6 are added to the syringe 12a so as to provide a prepared liquid sample S1. After that, a drive signal is again outputted to the pulse motor 12c, and thereby a predetermined amount (a+b+c+d) of the prepared liquid sample S1 is introduced from the syringe pump 12 to the reactor 40.

In the reactor 40, the prepared liquid sample S1 is irradiated with ultraviolet rays by means of the ultraviolet ray lamp 42 for approximately 20 minutes so that the nitrogen compounds are oxidatively decomposed into nitrate ions, and at the same time, potassium peroxydisulfate in the liquid is decomposed into potassium sulfate. After potassium peroxydisulfate has been entirely decomposed, a prepared liquid sample S1 is further irradiated with ultraviolet rays for 5 to 20 minutes so that nitrate ions are reduced into nitrite ions. After the completion of these reactions, the computer 160 outputs a drive signal to the pulse motor 12c, and thereby a predetermined amount (a+b+c+d) of the reacted liquid sample S2 is weighed and collected by the syringe pump 12. A drive signal is again outputted to the pulse motor 12c, and thereby a predetermined amount (e) of hydrochloric acid in the container 8 is added into the syringe 12a so as to generate a predetermined amount (a+b+c+d+e) of the prepared liquid sample S3.

Next, the computer 160 outputs a drive signal to the pulse motor 12c, and thereby the predetermined amount (a+b+c+d+e) of the prepared liquid sample S3 is introduced from the syringe pump 12 to the measuring cell 53. After that, a laser beam is emitted from the semiconductor laser element 51, and the light intensity I is detected by the photodiode 52. In addition, the computer 160 measures the absorbance at 220 nm on the basis of the detected light intensity I, and thus calculates the total nitrogen concentration in the prepared liquid sample S3.

3. Citation List

[Patent Literature]

Patent Literature 1: Japanese Unexamined Patent Publication 2003-344381

SUMMARY OF THE INVENTION

1. Technical Problem

As described above in the online total nitrogen measuring device 101, the amount of liquid in the sample tank 2 and the containers 3 through 11 may run short, or there may be an abnormality in a pipe, and thus, a necessary amount of solution may not be able to be collected by the syringe pump 12, or the prepared liquid sample S3 may leak during the process of being fed to the measuring cell 53 after being collected by the syringe pump 12. As a result, a predetermined amount (a+b+c+d+e) of the prepared liquid sample S3 may fail to be fed into the measuring cell 53.

In the online total nitrogen measuring device 101, however, the total nitrogen concentration of the liquid sample S is automatically calculated, and therefore, the analyst may not be able to find an abnormal state such as a shortage or leakage of the liquid, or such a finding may be delayed, resulting in the failure of the precise measurement of the total nitrogen concentration of the liquid sample S.

2. Solution to Problem

The present applicant examined the detection methods for finding an abnormal state in the online total nitrogen measuring device 101, and focused on the detection of whether or not a predetermined amount (a+b+c+d+e) of the prepared liquid sample S3 has been fed into the measuring cell 53. As for the method for detecting such an abnormality in the collection of water, detection of the existence of the prepared liquid sample S3 is possible by confirming the size of the transmissivity of light that has been detected by the photodiode 52 after the prepared liquid sample S3 has been fed into the measuring cell 53.

In the conventional online total nitrogen measuring device 101, however, the inside of the measuring cell 53 will not be hollow in the case where the amount of any type of liquid in the sample tank 2 and the containers 3 through 11 runs short. For example, in the case where a predetermined amount (d) of potassium peroxydisulfate solution fails to be added, and only an amount (a+b+c+e) of the prepared liquid sample S3' is fed into the measuring cell 53, it is determined to be "no problem." Accordingly, the detection method where it is determined whether or not the inside of the measuring cell 53 is hollow is insufficient.

Figure 5:
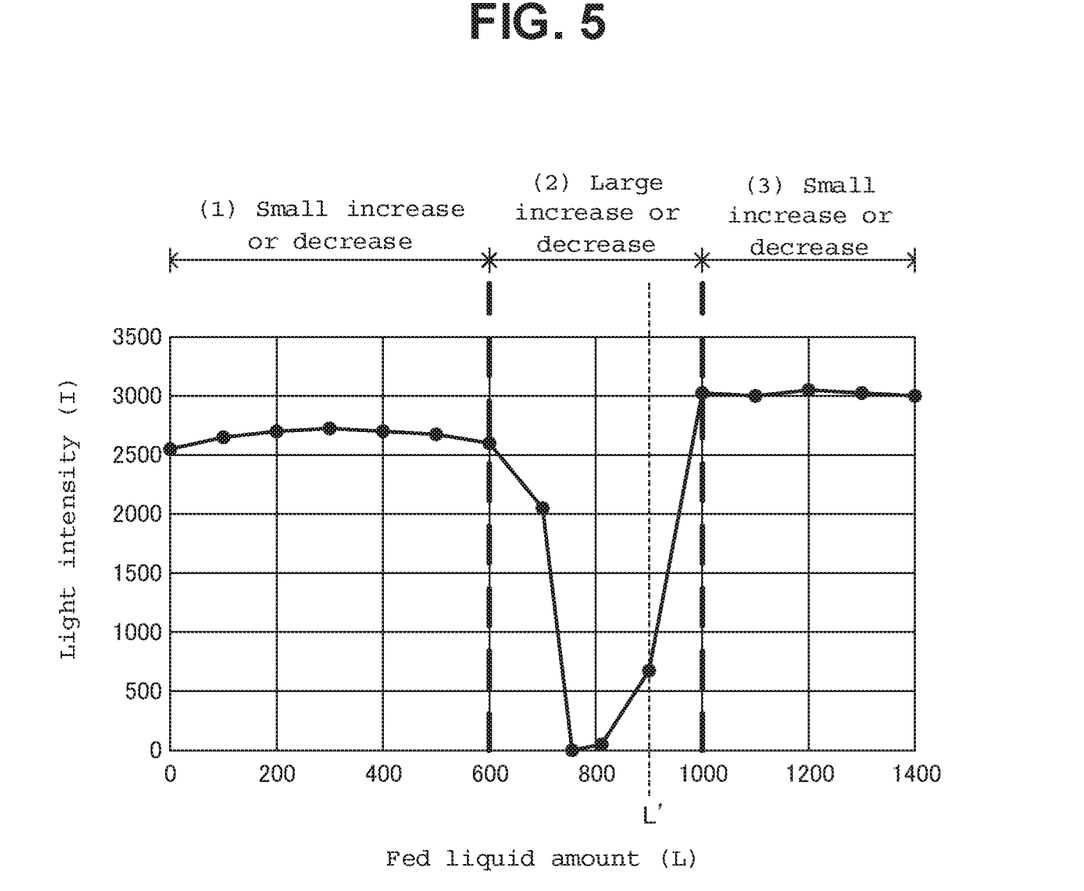
FIG. 5 is a graph showing an example of a change in the light intensity.

When the prepared liquid sample S3 is fed into the measuring cell 53 as described above, the successive state changes from (1) the state where the surface of the prepared liquid sample S3 layer has not reached the light path (region to be measured), to (2) the state where the surface of the prepared liquid sample S3 layer has reached the middle of the light path, and then to (3) the state where the light path is in the prepared liquid sample S3 layer. At this time, the prepared liquid sample S3 is fed into the measuring cell 53 while the semiconductor laser element 51 is turned on. Then, the change in the light intensity I(L) that is gained during the time when the state where the inside of the measuring cell 53 is hollow becomes the state where a predetermined amount (a+b+c+d+e) of the prepared liquid sample S3 is contained becomes a characteristic waveform relative to the amount L of the prepared liquid sample S3 that has been fed. As shown in FIG. 5, this waveform starts from (1) the "state where the increase or decrease in the light intensity I is small" relative to the amount M of the liquid that has been fed, passes through (2) and the "state where the increase or decrease in the light intensity I is large," and finally again becomes (3) the "state where the increase or decrease in the light intensity I is small."

In general, the measured amount of prepared liquid sample S3 that has been fed into the measuring cell 53 is uniquely determined by the type of measurement, and therefore, the fed liquid amount point L' where (2) the "state where the increase or decrease in the light intensity I is large" is gained is determined in the gained change in the light intensity I(L) in the case where the type of measurement (the fed liquid amount (a+b+c+d+e), for example) is determined. Therefore, in the case where (2) the "state where the increase or decrease in the light intensity I is large" is greater than the fed liquid amount point L' in the gained change in the light intensity I(L), or in the case where (1) the "state where the increase or decrease in the light intensity I is small" stays and does not become (2) the "state where the increase or decrease in the light intensity is large," the amount of liquid that has been fed into the measuring cell 53 is insufficient. That is to say, there is an abnormality in the collection of water during the process up to the feeding of the liquid into the measuring cell 53 after the weighing by the syringe pump 12.

Thus, it was found that an abnormality in the collection of water can be determined when the prepared liquid sample S3 is fed into the measuring cell 53 while the semiconductor laser element 51 is turned on, and the light intensity I at this time is monitored so as to find that the fed liquid amount L at the point where a relatively large fluctuation in the light intensity I has occurred is greater than the standard fed liquid amount L' or the light intensity I does not fluctuate.

That is to say, the water quality analyzer according to the present invention is provided with:

a sample container including a liquid sample introduction port formed in its lower portion, and the sample container configured to receive a predetermined amount of liquid sample introduced through the liquid sample introduction port; a light source unit for irradiating said sample container with light; a detection unit for detecting light that has passed through said sample container; and a determination unit for determining whether or not a predetermined amount of liquid sample has been contained in said sample container based on the varying light intensity detected by said detection unit, the variance of the light intensity caused by a liquid sample fed into said sample container.

Here, the "predetermined amount" is any amount for measuring the absorbance or the like of the liquid sample that has been predetermined by an analyst or the like.

3. Advantageous Effects of the Invention

As described above, the water quality analyzer according to the present invention can allow an abnormal state due to a shortage or leakage of liquid to be quickly found.

4. Other Solutions to Problem and Advantageous Effects Thereof

In addition, in the water quality analyzer according to the present invention, the above-described sample container may be a measuring cell for analyzing the liquid sample or a reaction container for making the liquid sample react.

Furthermore, the water quality analyzer according to the present invention may be provided with a weighing unit for weighing the liquid sample, a valve to which the liquid sample introduction port and the above-described weighing unit are connected, and a control unit for controlling the above-described weighing unit and the above-described valve.

DETAILED DESCRIPTION OF EMBODIMENTS

In the following, the embodiments of the present invention are described in reference to the drawings. Here, the present invention is not limited to the embodiments as described below, and needless to say, includes various modifications as long as the gist of the present invention is not deviated from.

Figure 1:
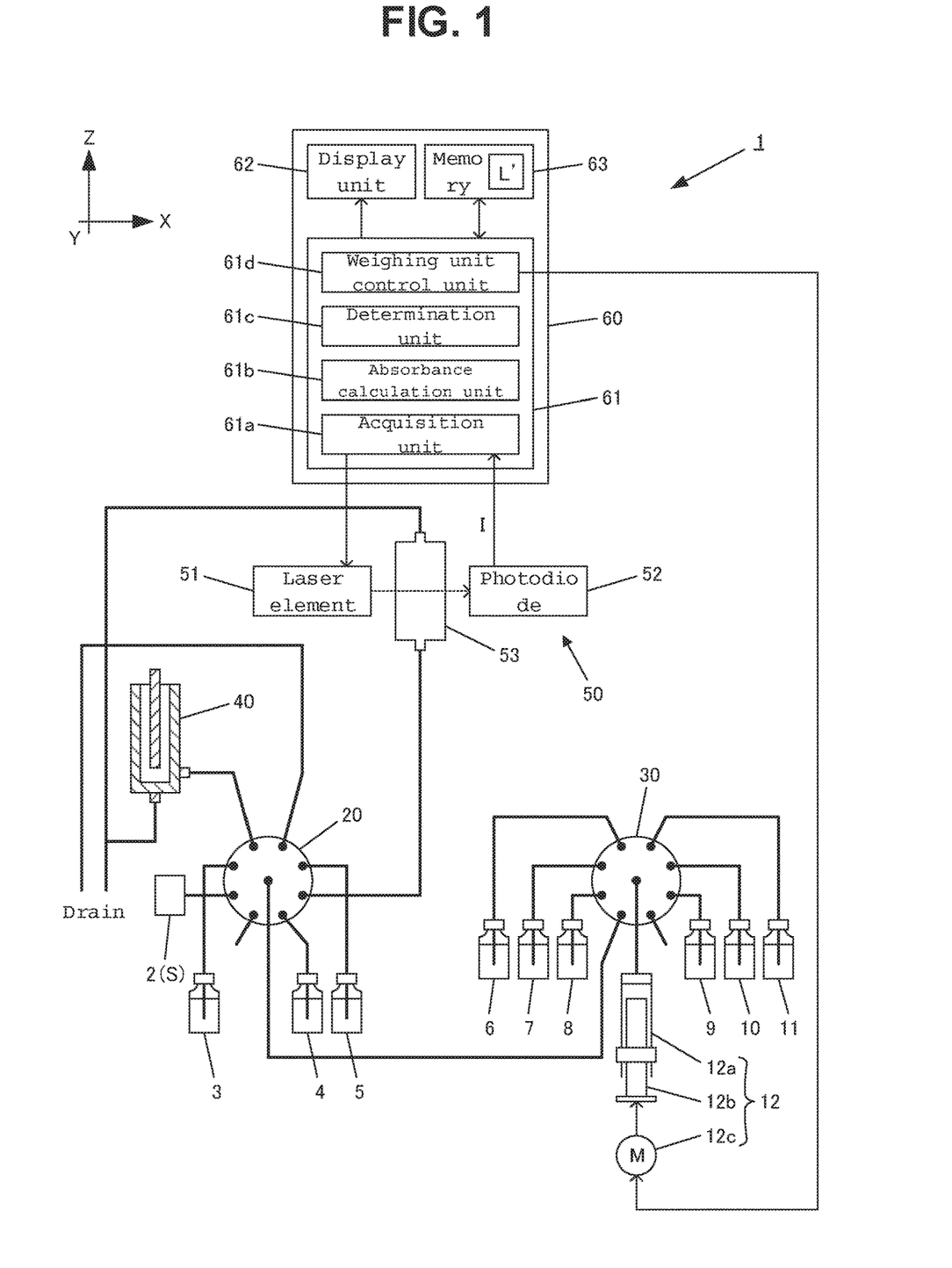
FIG. 1 is a schematic diagram showing the entire configuration of an example of the total nitrogen measuring device according to the present invention.

FIG. 1 is a schematic diagram showing the entire configuration of an online total nitrogen measuring device as an example of the water quality analyzer according to the present invention. Here, the same symbols are attached to the similar components as in the above-described online total nitrogen measuring device 101, and the descriptions thereof are not repeated.

An online total nitrogen measuring device 1 is provided with a sample tank 2, a syringe pump (weighing unit) 12, a first multiport valve 20, a second multiport valve 30, a reactor 40, a measuring unit 50 and a computer 60.

The computer 60 is provided with a CPU (control unit) 61, a display unit 62 such as a monitor, and a memory 63. In addition, the functions that are processed by the CPU 61 are described using the blocks, which are an acquisition unit 61a for acquiring the light intensity I from a photodiode (detection unit) 52, an absorbance calculation unit 61b for calculating the absorbance on the basis of the detected light intensity I, a determination unit 61c for determining whether or not a predetermined amount of the prepared liquid sample S3 has been contained on the basis of the change in the light intensity I(L), and a weighing unit control unit 61d for controlling the syringe pump 12.

Furthermore, in order to determine an abnormality in the collection of water, the memory 63 stores in advance a standard liquid amount to be fed L' (900 µl, for example) that provides the state where "(2) an increase or decrease in the light intensity I is relatively large" when a predetermined amount (a+b+c+d+e) of the prepared liquid sample S3 is fed.

The determination unit 61c controls the system so as to determine whether or not a predetermined amount (a+b+c+d+e) of the prepared liquid sample S3 has been contained within the measuring cell 53 on the basis of the change in the light intensity I(L) detected by the photodiode 52 when the prepared liquid sample S3 is contained within the measuring cell 53.

Concretely, the amount of inclination in the curve of the change in the light intensity I(L) detected by the photodiode 52 is sequentially checked when the reacted liquid sample S2 is contained within the measuring cell 53. When the amount of inclination becomes a predetermined value or less, it is determined to be the starting point of a peak. When the amount of inclination is changed from negative to positive, it is determined to be the peak (fed liquid amount point L). When the amount of inclination becomes a predetermined value or less, it is determined to be the end point of the peak. In the case where the fed liquid amount point L is greater than the standard fed liquid amount L', it is determined that the amount of the liquid fed into the measuring cell 53 runs short, and a warning is displayed on the display unit 62. In the case where no peak has been detected as well, it is determined that the amount of the liquid fed into the measuring cell 53 runs short, and a warning is displayed on the display unit 62.

Here, the method for automatically analyzing the total nitrogen concentration of a liquid sample S by using the above-described online total nitrogen measuring device 1 is described. The weighing unit control unit 61d of the computer 60 outputs a drive signal to the pulse motor 12c in accordance with a predetermined timing so that a predetermined amount (a) of the liquid sample S is weighed and collected from the sample tank 2 by means of a syringe pump 12. A drive signal is again outputted to the pulse motor 12c so that a predetermined amount (b) of diluent water is weighed and collected from the container 5 by means of the syringe pump 12 so as to dilute the liquid sample S within the syringe 12a. Next, the weighing unit control unit 61d outputs a drive signal to the pulse motor 12c so that a predetermined amount (c) of a sodium hydroxide solution is added from the container 7 into the syringe 12a, and a predetermined amount (d) of a potassium peroxydisulfate solution is added from the container 6 into the syringe 12a so as to provide a prepared liquid sample S1. After that, a drive signal is again outputted to the pulse motor 12c so that a predetermined amount (a+b+c+d) of the prepared liquid sample S1 is introduced from the syringe pump 12 to the reactor 40.

In the reactor 40, the prepared liquid sample S1 is irradiated with ultraviolet rays from the ultraviolet ray lamp 42 for approximately 20 minutes so as to oxidatively decompose the nitrogen compounds into nitrate ions, and at the same time decompose the potassium peroxydisulfate in the liquid into potassium sulfate. After all the potassium peroxydisulfate has been decomposed, the liquid is further irradiated with ultraviolet rays for 5 to 20 minutes so as to reduce the nitrate ions into nitrite ions. After the completion of these reactions, the weighing unit control unit 61d outputs a drive signal to the pulse motor 12c so that a predetermined amount (a+b+c+d) of the reacted liquid sample S2 is weighed and collected by means of the syringe pump 12. A drive signal is again outputted to the pulse motor 12c so that a predetermined amount (e) of hydrochloric acid is added from the container 8 into the syringe 12a so as to generate a predetermined amount (a+b+c+d+e) of the prepared liquid sample S3.

Next, the weighing unit control unit 61d outputs a drive signal to the pulse motor 12c so that a predetermined amount (A+b+c+d+e) of the prepared liquid sample S3 is introduced from the syringe pump 12 to the measuring cell 53. At this time, the acquisition unit 61a allows the semiconductor laser element 51 to emit a laser beam so as to allow the photodiode 52 to detect a change I(L) in the light intensity. Next, the determination unit 61c determines whether or not a predetermined amount (a+b+c+d+e) of the prepared liquid sample S3 has been contained in the measuring cell 53 on the basis of the detected change I(L) in the light intensity.

In the case where it is determined that a predetermined amount (a+b+c+d+e) of the prepared liquid sample S3 has been contained, the absorbance calculation unit 61b measures the absorbance at 220 nm on the basis of the detected light intensity I so that the total nitrogen concentration in the liquid sample S is calculated and stored in the memory 63. Meanwhile, in the case where it is determined that a predetermined amount (a+b+c+d+e) of the prepared liquid sample S3 has not been contained, the determination unit 61c displays a warning on the display unit 62.

As described above, the online total nitrogen measuring device 1 that has the configuration according to the present invention makes it possible to find an abnormal state such as running short of a liquid or a liquid leakage at an early stage.

<Other Embodiments>

<1> In the above-described online total nitrogen measuring device 1, a configuration where it is determined whether or not a predetermined amount (a+b+c+d+e) of the prepared liquid sample S3 has been contained within the measuring cell 53 is shown. Instead of this, however, a configuration may be provided where a light source unit and a detection unit are provided in the reactor 40 in such a manner that it is determined whether or not a predetermined amount (a+b+c+d+e) of the prepared liquid sample S1 has been contained within the reactor 40.

<2> Though the configuration in the above-described embodiment relates to a case where the present invention is applied to the online total nitrogen measuring device 1, the configuration may relate to a case where the invention is applied to another water quality analyzer instead.

INDUSTRIAL APPLICABILITY

The present invention can be applied to a water quality analyzer such as a total nitrogen measuring device for measuring the total nitrogen concentration in a liquid sample.

REFERENCE SIGNS LIST

1: online total nitrogen measuring device (water quality analyzer)
51: semiconductor laser element (light source unit)
52: photodiode (detection unit)
53: measuring cell (sample container)
53e: liquid sample introduction port
61c: determination unit

What is claimed is:

1. A water quality analyzer, comprising:
a sample container including a liquid sample introduction port formed in its lower portion, the sample container configured to receive a predetermined amount of liquid sample introduced through the liquid sample introduction port;
a light source for irradiating the sample container with light;
a detector for detecting light passing through the sample container, wherein a reference change, in light intensity is detected by the detector when the predetermined amount of liquid sample is introduced into the sample container;

a first valve and a second valve connected to each other to introduce the predetermined amount of liquid sample into the sample container;

the first valve connected to the liquid sample introduction port;

the second valve connected to a syringe pump;

a memory storing the reference change in light intensity; and a processor comprising program code configured to;

determine whether or not the predetermined amount of liquid sample is contained in the sample container based on an actual change in light intensity detected by the detector when the sample liquid is stored in the sample container, and by comparing the detected actual change in light intensity with the reference change in light intensity;

and wherein the program code further comprises;

weighing code configured to cause the processor to control the syringe pump to weigh and collect the predetermined amount of liquid sample before introduction into the sample container; and control code configured to cause the processor to control the weighing code and the first and second valves.

2. The water quality analyzer according to claim 1, wherein the sample container is a measuring cell for analyzing the liquid sample or a reaction container for causing a reaction in the liquid sample.

3. The water quality analyzer according to claim 1, wherein a position of a target region to be measured by the light source and the detector is arranged above the liquid sample introduction port.

4. The water quality analyzer according to claim 1, wherein the water quality analyzer further comprises a display configured to display an amount of liquid fed into the sample container and display a message based on a change of light intensity of the light passing through the sample container.

* * * * *